(12) United States Patent
Yankelson et al.

(10) Patent No.: US 8,703,119 B2
(45) Date of Patent: Apr. 22, 2014

(54) INJECTABLE BIODEGRADABLE POLYMER COMPOSITIONS FOR SOFT TISSUE REPAIR AND AUGMENTATION

(75) Inventors: Lior Yankelson, Tel Aviv (IL); Abraham J. Domb, Efrat (IL)

(73) Assignee: Polygene Ltd., Efrat (IL)

( * ) Notice: Subject to any disclaimer, the term of this patent is extended or adjusted under 35 U.S.C. 154(b) by 125 days.

(21) Appl. No.: 12/678,492

(22) PCT Filed: Oct. 5, 2008

(86) PCT No.: PCT/IL2008/001320
§ 371 (c)(1),
(2), (4) Date: Apr. 5, 2010

(87) PCT Pub. No.: WO2009/044403
PCT Pub. Date: Apr. 9, 2009

(65) Prior Publication Data
US 2010/0260703 A1      Oct. 14, 2010

Related U.S. Application Data

(60) Provisional application No. 60/977,991, filed on Oct. 5, 2007.

(51) Int. Cl.
*A61K 31/765*   (2006.01)
*A61P 13/00*    (2006.01)
*A61P 17/00*    (2006.01)
*A61F 2/02*     (2006.01)

(52) U.S. Cl.
USPC .................................. 424/78.37; 623/23.72

(58) Field of Classification Search
USPC .................................................. 424/59, 486
See application file for complete search history.

(56) References Cited

U.S. PATENT DOCUMENTS

| | | | |
|---|---|---|---|
| 4,235,312 A | 11/1980 | Garrett | |
| 4,664,655 A | 5/1987 | Orentreich | |
| 4,758,234 A | 7/1988 | Orentreich | |
| 4,938,763 A | 7/1990 | Dunn | |
| 5,278,201 A | 1/1994 | Dunn | |
| 5,278,202 A | 1/1994 | Dunn | |
| 5,278,203 A | 1/1994 | Harms | |
| 5,387,658 A | 2/1995 | Schroder | |
| 5,827,937 A | 10/1998 | Agerup | |
| 6,444,782 B1 | 9/2002 | Hamlin | |
| 6,540,987 B2 * | 4/2003 | Weipert et al. | 424/59 |
| 6,905,820 B2 | 6/2005 | Uhlmann | |
| 6,977,263 B2 | 12/2005 | Astles | |
| 7,294,347 B2 | 11/2007 | Menjoge | |
| 7,297,347 B2 | 11/2007 | Domb | |
| 2002/0025340 A1 * | 2/2002 | Dyer | 424/486 |
| 2004/0057970 A1 | 3/2004 | Domb | |
| 2004/0161464 A1 | 8/2004 | Domb | |
| 2005/0009073 A1 | 1/2005 | Uhlmann | |
| 2005/0226936 A1 | 10/2005 | Agerup | |
| 2005/0228018 A1 | 10/2005 | Astles | |
| 2007/0036855 A1 | 2/2007 | Domb | |
| 2007/0110788 A1 | 5/2007 | Hissong | |
| 2008/0070258 A1 | 3/2008 | Uhlmann | |
| 2008/0312739 A1 | 12/2008 | Agerup | |
| 2010/0068252 A1 | 3/2010 | Anthasius | |
| 2010/0184635 A1 | 7/2010 | Tollington | |
| 2010/0186764 A1 | 7/2010 | Pasquet | |

FOREIGN PATENT DOCUMENTS

| | | |
|---|---|---|
| EP | 0547897 | 6/1993 |
| EP | 0839159 | 8/2001 |
| EP | 01354586 | 10/2003 |
| EP | 01212269 | 10/2004 |
| EP | 01499312 | 3/2007 |
| EP | 01051397 | 12/2008 |
| EP | 2002853 | 12/2008 |
| WO | WO9938844 | 8/1999 |
| WO | WO0244232 | 6/2002 |
| WO | WO03088966 | 10/2003 |
| WO | WO2004073759 | 9/2004 |
| WO | WO2004110530 | 12/2004 |

(Continued)

OTHER PUBLICATIONS

Sokolsky-Papkov et al., "Polymer carriers for drug deliver in tissue engineering". Advanced Drug Delivery Reviews 2007:59;187-206.*

(Continued)

*Primary Examiner* — Walter Webb
(74) *Attorney, Agent, or Firm* — Graeser Associates International Inc; Dvorah Graeser

(57) ABSTRACT

Methods for soft tissue repair and/or augmentation using injectable, biodegradable polymers are described herein. In one embodiment, the polymer compositions are liquid or pastes at room temperature. In a preferred embodiment, the polymer composition contains liquid or pasty hydroxy fatty acid-based copolyesters, polyester-anhydrides, or combinations thereof. The viscosity of the polymers increases upon contact with bodily fluid to form a solid or semisolid implant suitable for soft tissue repair and/or augmentation. In another embodiment, the polymer composition contains particles of a polymer stereocomplex. One or more active agents may be incorporated into the polymer compositions. Suitable classes of active agents include local anesthetics, anti-inflammatory agents, antibiotics, analgesics, growth factors and agents that induce and/or enhance growth of tissue within the filled cavity or control the growth of a certain type of tissue, and combinations thereof. The polymer compositions may also contain one or more additives or excipients that modify the physical and/or mechanical properties of the polymer. The polymer compositions are typically administered by injection. The injectable polymers can be used for a variety of soft tissue repair and augmentation procedures.

13 Claims, 4 Drawing Sheets

(56) References Cited

FOREIGN PATENT DOCUMENTS

| WO | WO2005073284 |   | 8/2005  |           |
|----|--------------|---|---------|-----------|
| WO | WO2005097218 |   | 10/2005 |           |
| WO | W02005105037 |   | 11/2005 |           |
| WO | WO 2006/078725 | * | 7/2006 | C08G 63/00 |
| WO | WO2006078725 |   | 7/2006  |           |
| WO | WO2007005489 |   | 1/2007  |           |
| WO | WO2007110694 |   | 10/2007 |           |
| WO | WO2010144392 |   | 12/2010 |           |

OTHER PUBLICATIONS

Boccaccini et al., "Preparation and characterisation of poly(lactide-co-glycolide) (PLGA) and PLGA/Bioglass composite tubular foam scaffolds for tissue engineering applications." Materials Science and Engineering 2005:C 25;23-31.*

International search report and written opinion for corresponding PCT/IL2008/001320 dated Oct. 5, 2008.

Krasko, M. Y., et al., Poly (ester anhydride)s prepared by the insertion of ricinoleic acid into poly (sebacic acid), J. Polym. Sci Pol. Chem., 2003, 41 (8), 1059-1069.

Teomim,d; et al; "Ricinoleic acid-based biopolymers", J. Biomed. Mater. Res. 1999, 45, 258-267.

Slivniak, R. Et al; "Macrolactones and polyesters from ricinoleic acid", Biomacromolecules, 2005, 6, 1679-88.

Slivniak, R. et al; "Hydrolytic degradation and drug release of ricinoleic acid-lactic acid copolyesters", Pharm Res., 2006, 23, 1306-12.

Marlna, S. et al; "Fatty acid based biodegradable polymers-synthesis and applications",Bulletin of the Israel Chemical Society, 2008, 23, 12-17.

Marina, S. et al; "Prolonged Local Anesthetic Action Through Slow Release from Poly (Lactic Acid Co Castor Oil)", Pharmaceutical Researah, vol. 26, No. 1, 2009, 31-39.

Ravi, K, et al; "Study of Paracetamol Release from a Castor Oil Based Copolyester Matrix" Iranion Polymer vol. 5, No. 1, 1996, 60-64.

* cited by examiner

INJECTABLE BIODEGRADABLE POLYMER COMPOSITIONS FOR SOFT TISSUE REPAIR AND AUGMENTATION

CROSS-REFERENCE TO RELATED APPLICATIONS

This Application is a national phase of, and claims priority from, PCT Application No. PCT/IL2008/001320, filed on Oct. 5, 2008, which claims priority from U.S. Provisional Application No. 60/977,991, filed on Oct. 5, 2007, all of which are hereby incorporated by reference as if fully set forth herein.

FIELD OF THE INVENTION

The invention is in the field of polymeric compositions for soft tissue repair and augmentation, particularly polymer compositions which can be administered by injection.

BACKGROUND OF THE INVENTION

The repair or augmentation of soft tissue defects or contour abnormalities caused by facial defects, acne, surgical scarring or aging has proven to be very difficult. A number of materials have been used to correct soft tissue defects with varying degrees of success, but currently no material appears to be completely safe and effective. In the past, small amounts of liquid silicone were used to correct minor soft tissue defects where minimal mechanical stress was present at the recipient site. Unfortunately, liquid silicone from these injections appears to migrate to distant body parts and can cause a variety of physiological and clinical problems. In response to these problems and the misuse of liquid silicone, the FDA has prohibited the use of liquid silicone in humans.

In the 1970's, reconstituted injectable bovine collagen became available as a potential treatment for soft tissue defects. However, over time, the benefits of collagen treatment have proven to be short-lived as the collagen reabsorbs in two to three months. Additionally, safety measures must be employed with this material to avoid allergic reactions to the bovine proteins in the collagen. In an attempt to solve these shortcomings, crosslinked collagen was introduced to extend effective treatment times to approximately six months. However, allergic reactions still occur with the crosslinked collagen material and frequent readministration of the crosslinked material is still required for efficacy.

Recently, several groups have investigated other materials that may be used for soft tissue repair or augmentation such as biocompatible ceramic particles in aqueous gels, thermoplastic materials, thermosetting materials and lactic acid based polymer blends, to overcome some of the problems previously experienced with collagen and liquid silicone.

Injectable implants containing biocompatible ceramic particles in an aqueous gel are described in U.S. Pat. No. 5,204,382 to Wallace et al. The implants consist of ceramic particles of calcium phosphate from a nonbiological source, mixed with an aqueous gel carrier in a viscous polymer (such as polyethylene glycol, hyaluronic acid, poly(hydroxyethyl methacrylate) and collagen). Although these materials are generally nontoxic, there appears to be risks associated with the use of nonabsorbable particulate materials related to the migration of these particles to distance sites in the body.

Injectable polymeric systems have also been reported. For example, hydrophilic solutions of a polymer in water or N-methylpyrrolidone (NMP) which form an implant as a result of diffusion of the solvent or water from the polymer solution have been investigated. However, the diffusion of the solvent or water reduces the size of the injected polymer, resulting in a composition which is not suitable as a filler for skin repair or augmentation (Y. J. Kim, *Pharm. Res.*, 18(4) 548-550 (2001)).

Thermoplastic and thermosetting defect fillers are described in U.S. Pat. Nos. 4,938,763, 5,278,201 and 5,278,202 to Dunn et al. Dunn describes the use of both a thermoplastic material with a solvent and a thermosetting material with a curing agent to form solid implants in situ. Although the biodegradable materials proposed for use as thermoplastics appear to be biocompatible, the solvents necessary to dissolve them for injection into tissue may not be biocompatible. Additionally, the thermoplastic and thermosetting materials have limited utility in filling soft tissue because they solidify. Similar commercially available materials exhibit ultimate yield stresses of approximately 10,000 psi; in comparison, human skin exhibits ultimate yield stresses of from 500 to 2,000 psi. Therefore, due to palpability concerns, the thermoplastic and thermosetting materials described appear to be too hard for use in soft tissue augmentation or repair and especially in dermal augmentation or repair.

Soft tissue repair or augmentation has also been proposed using lactic acid-based polymer blends of amorphous oligomers with crystalline oligomers or polymers (see U.S. Pat. No. 4,235,312 to Buchholz et al.). These blends were developed to provide a pasty or waxy material which could be used as an absorbable implant to replace the brittle copolymers of lactic acid and glycolic acid already known for use as bone waxes. However, these blends do not appear to be suitable for use as injectable soft tissue defect fillers, because they are too viscous to be injected through a needle which significantly limits the utility of these blends. Furthermore, the low molecular weight liquid oligomers described in the '312 patent are slightly soluble in body fluids, which means that these oligomers will quickly diffuse out of the site of implantation to other areas of the body.

In view of the deficiencies of the soft tissue augmentation materials previously considered, there exists a need for soft tissue augmentation materials with improved mechanical properties. Ideally, any augmentation material would have several important characteristics not possessed by the prior art materials. For example, any soft tissue augmentation material should be completely biodegradable to avoid the possibility of long-term chronic irritation of tissues or migration of nonabsorbable materials over time to different areas of the body. The soft-tissue augmentation materials should also provide soft tissue augmentation for at least six months to avoid frequent readministration of the augmentation material. Furthermore, soft tissue augmentation materials should be of very low viscosity or particle size to allow easy administration by injection using a thin gauge needle (e.g., 27-30 G). Finally, the ideal soft tissue augmentation material would have the appropriate degree of pliability and viscosity for the tissue into which the new material was being implanted to provide life-like tissue augmentation or repair. As discussed above, none of the currently available materials have all of these characteristics.

Therefore, it is an object of the invention to provide injectable biocompatible, biodegradable polymer compositions suitable for soft tissue augmentation and/or repair, and methods of making and using thereof.

SUMMARY OF THE INVENTION

Methods for soft tissue repair and/or augmentation using injectable, biodegradable polymers are described herein. In one embodiment, the polymer compositions are liquid or pastes at room temperature. In a preferred embodiment, the polymer composition contains liquid or pasty polyesters, polyester-anhydrides, or combinations thereof. The polymers can be made by a variety of methods known in the art, such as condensation or ring opening polymerization, of hydroxyl fatty acids, such as castor oil, vernonia oil and their corresponding fully or partially hydrolyzed or reduced products such as ricinoleic acid, hydroxyl-stearic acid and mono and diglycerides thereof, and esters thereof with one or more polyfunctional organic molecules including, but not limited to, short hydroxyl alkanoic acids and their corresponding lactones, di and trimethylene carbonates, amino acids, or di- or polycarboxylic acids.

The liquid or pasty polymer compositions should be sufficiently viscous to be injected into tissue using a syringe with a small gauge needle, for example 27-30 gauge. In one embodiment, the polymer composition is a liquid at room temperature which can be injected neat (i.e., without a solvent). In another embodiment, the polymer composition is a paste at room temperature. The pasty polymer can be injected neat or in combination with a pharmaceutically acceptable, water-miscible solvent that sufficiently reduces the viscosity of the pasty polymer to allow for administration by injection. The viscosity of the liquid polymers may vary depending on the molecular weights of the liquid copolymers as well as on the composition of the polymers. Generally, the viscosity of the liquid copolymers will be less than 10,000 poise and preferably will be in the range of from about 20 poise to about 2,000 poise as determined by capillary rheometry. Upon administration, the viscosity of the polymer increases so that the polymer, for example, to ensure that the polymer remains in place. In one embodiment, the viscosity of the polymer increases at least two fold to form, for example, a semisolid or solid material.

In another embodiment, the polymer composition is in particulate form, where the biodegradable polymer is a stereocomplex. In one embodiment, the stereocomplex is formed from the stereocomplexation of stereoregular polymers including polyesters of α-hydroxy acids, such as D-polylactide and L-polylactide and their copolymers, and polyamides of α-amino acids. In a preferred embodiment, the stereocomplex is formed from the stereocomplexation of stereoregular lactic acid homo or block copolymers. The particles can be dispersed in a pharmaceutically acceptable carrier, such as water or an aqueous solvent or cosolvent and administered by injection.

The liquid, pasty, and particulate polymers should be stable during storage and should degrade at a pre-determined time period from about three weeks to three years, preferably from about three weeks to about two years, and fully eliminated from the body, without causing adverse side effects. In a preferred embodiment, the compositions degrade in vivo over a period of about 18 months. The compositions should be stable for at least one year at room temperature and at least three years when stored under freezing conditions. The degradation profile and/or mechanical properties of the polymer can also be controlled by the application of external stimuli; such as ultrasound, local heating by RF or light, iontophoresis, electrical current, and combinations thereof.

One or more active agents may be incorporated into the polymer compositions. Suitable classes of active agents include, but are not limited to, local anesthetics, anti-inflammatory agents, antibiotics, analgesics, growth factors and agents that induce and/or enhance growth of tissue within the filled cavity or control the growth of a certain type of tissue, such as certain types of collagen, and combinations thereof.

The polymer compositions may also contain one or more additives or excipients that modify one or more properties of the polymer.

The polymer compositions are typically administered by injection, for example, via a prefilled syringe loaded with the polymer composition with a fixation point for the needle (i.e., a luer lock) and a set of needles with various gauges suitable for various applications. For deep implantation in the body, the syringe may be connected to a tube or catheter fitted to the outlet for administering the liquid polymers into a site within the body. An automated injector may be used for better control of the injection of the polymer formulations. The injectable polymer can be used for a variety of soft tissue repair and augmentation procedures, such as facial tissue repair, to improve sphincter function, or for treating incontinence or other bladder disorders.

DETAILED DESCRIPTION OF THE INVENTION

I. Definitions

Figure 1:
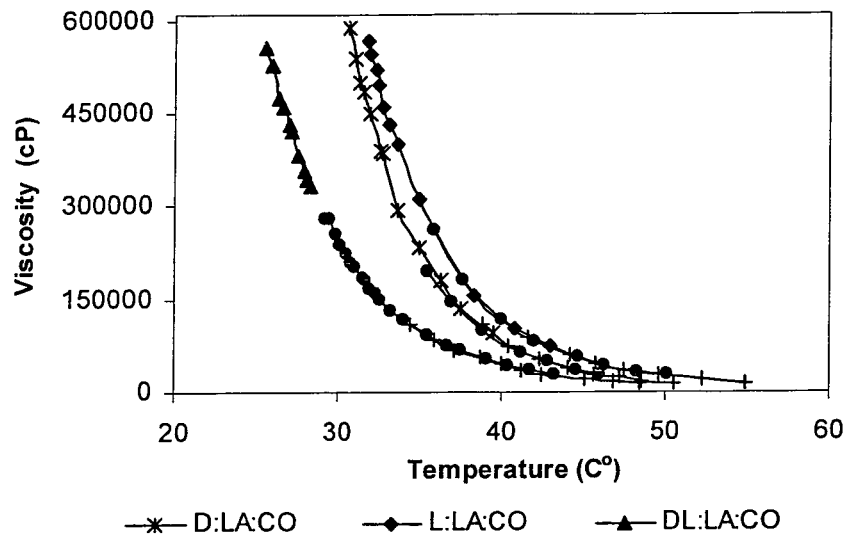
FIG. 1 is a graph showing the viscosity (cP) of three different poly(lactide-co-castor oil) copolymers: poly(D-lactide-co-castor oil) (*), poly(L-lactide-co-castor oil) (♦), and poly(DL-lactide-co-castor oil) (▲) having a 7:3 ratio of lactide to castor oil as a function of temperature (° C.).

"Needle", as used herein, refers to devices that can be used to administer, deliver, inject, or otherwise introduce the polymer compositions to a subject for tissue repair and/or augmentation. Thus, as defined herein, needle includes needle, all needle-like devices, and all other annular introduction devices, such as tubing, etc. Specific examples include needles, hypodermic needles, surgical needles, infusion needles, catheters, trocars, cannulas, tubes, and tubing used for clinical, surgical, medical, procedural, or medical purposes.

"Injected", "injection", or "injectability" as used herein is intended to include any administration of the polymer composition, such as by injection, infusion, or any other delivery through any annular delivery device to the subject. Injection includes delivery through a tube.

The term "gauge" refers to the needle size in terms of a gauge scale. Smaller gauge numbers refer to larger diameter needles. The polymer composition is typically administered through a small gauge needle (e.g., 27-30 gauge). However, needles with a larger or smaller gauge can be used depending on the application.

As used herein, a "wt. %" or "weight percent" or "percent by weight" of a component, unless specifically stated to the contrary, refers to the ratio of the weight of the component to the total weight of the composition in which the component is included, expressed as a percentage.

As used herein, a "mole percent" or "mole %" of a component, unless specifically stated to the contrary, refers to the ratio of the number of moles of the component to the total number of moles of the composition in which the component is included, expressed as a percentage.

"Admixture," "mixture," or "blend" is generally used herein to refer to a physical combination of two or more different components. In the case of polymers, an admixture, mixture, or blend of polymers is a physical blend or combination of two or more different polymers. The mixture may be homogeneous or heterogeneous.

"Copolymer" is used herein to refer to a single polymeric material that is comprised of two or more different monomers. The copolymer can be of any form, such as random, block, graft, etc. The copolymers can have any end-group, including capped or acid end groups.

"Soft tissue", as used herein, refers non-skeletal tissue, i.e. exclusive of bones, ligaments, cartilage, spinal disc and fibrous tissue.

"Biocompatibility" or "biocompatible", as generally used herein, refers to the ability of a material to perform with an appropriate host response in a specific application. In the broadest sense, this means a lack of adverse effects to the body in a way that would outweigh the benefit of the material and/or treatment to the patient.

"Tissue augmentation", as used herein, means the act of augmenting, filling gaps and making by addition and increase of material. Furthermore, it means the state of being augmented. For example, as used herein augmentation means in particular to strengthen and/or smooth tissue, such as skin or to repair scarred tissue, such as scarred skin. Augmentation can also encompass cementation of artificial joints like artificial hips and knees within the body or filling voids (e.g., increasing volume) in various parts of the body, such as joints.

"Physiological conditions", as used herein, means conditions as they can be found in living vertebrates. In particular, physiological conditions refer to the conditions in the human body such as temperature, pH, etc. "Physiological temperature" means in particular a temperature range of between 35° C. to 42° C., preferably around 37° C.

"Physiological fluids", as used herein, refers to fluids found in living vertebrates. "Physiological fluids" typically refers to liquids, but may include gases or suspensions. Examples of "physiological liquids" include, but are not limited to, blood, plasma, cerebrospinal fluid, urine, lymph, gastric juices, synovial fluid, and sputum.

"Tissue repair", as used herein, refers to physically filling gaps or voids in tissue. Tissue repair also refers to manipulating the size, appearance, and/or function of tissue "Biodegradable" refers to a material that will degrade or erode under physiologic conditions to smaller units or chemical species that are capable of being metabolized, eliminated, or excreted by the subject. The polymers can be degraded hydrolytically or enzymatically.

"Molecular weight" as used herein, unless otherwise specified, refers to the relative average chain length of the bulk polymer. In practice, molecular weight can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

"Mean particle size" refers to the statistical mean particle size (diameter) of the particles in the composition.

"Controlled release" or "modified release", as used herein, refers to a release profile in which the drug release characteristics of time course and/or location are chosen to accomplish therapeutic or convenience objectives not offered by conventional dosage forms such as solutions, suspensions, or promptly dissolving dosage forms. Delayed release, extended release, and pulsatile release and their combinations are examples of modified release.

"Excipient" is used herein to include any other compound that can be contained in the composition that is not a therapeutically or biologically active compound. As such, an excipient should be pharmaceutically or biologically acceptable or relevant, for example, an excipient should generally be non-toxic to the subject. "Excipient" includes a single such compound and is also intended to include a plurality of compounds.

"Polyfunctional organic molecule", as used herein, refers to an organic molecule containing two or more reactive functional groups. Suitable reactive functional groups include, but are not limited to, hydroxyl groups, carboxylic acid groups, and amino groups. Examples of polyfunctional organic molecules include, but are not limited to, hydroxy alkanoic acids, hydroxy fatty acids, amino acids, di- and polycarboxylic acids, dihydroxy alkanes, diamino alkanes, hydroxyamino alkanes.

"Increase in viscosity", as used herein, refers to a measurable increase in viscosity of the injected formulation after administration in tissue. For example, the increase in the viscosity can cause the composition to convert from a paste to a semisolid (e.g., a gel) or a liquid to a semisolid (e.g., a gel).

"Stereocomplex", as used herein, refers to a specific interaction between two stereoselective polymers of complementing structure that interlock into a composite that possesses different physical properties from the individual polymers. To form a stereocomplex, the stereoselective polymers must contain chiral segments that have opposite chirality. The complementing polymers can be two enantiomeric, optically active, polymer chains with identical chemical composition or two optically active polymers that have a similar but not identical chemical structure. In the latter case the polymers relate to each other as diastereomers. For example, in the case of two polymers, where one contains blocks of D-PLA and the other contains L-PLA segments, the D-blocks of one polymer will stereocomplex with an L-blocks of the second polymer when mixed. The resulting polymer stereocomplex is insoluble in the solvent that dissolved the original polymers (i.e. acetonitile) and melts at a higher temperature (>30° C.). Also, its degradation profile is different from the starting polymers.

"Active agent" includes without limitation, physiologically or pharmacologically active substances that act locally or systemically in the body. A biologically active agent is a substance used for the treatment, prevention, diagnosis, cure or mitigation of disease or illness, a substance which affects the structure or function of the body, or pro-drugs, which become biologically active or more active after they have been placed in a predetermined physiological environment.

"Stiffness" is defined as measure of resistance of a material to bending. It includes both plastic and elastic behavior. Stiffness of the compositions is typically determined by measurement of the Young's modulus E.

"Strain" is change per unit length in a linear dimension of a part or specimen, usually expressed in % strain based on original length of the specimen ($\Delta L/L_o$). True or natural strain is based on instantaneous length, and is equal to In×lo, where l is instantaneous length and lo is original length of the specimen. Shear strain is the change in angle between two lines originally at right angles.

"Stress" is defined as load on specimen divided by the area through which it acts and generally contains units of Pa or MPa. As used with most mechanical tests, stress is based on original cross-sectional area without taking into account changes in area due to applied load. This sometimes is called conventional or engineering stress. True stress is equal to the load divided by the instantaneous cross-sectional area through which it acts.

"Modulus of Elasticity/Young's modulus E" is defined as the rate of change of strain as a function of stress and generally contains units of Pa or MPa. Young's Modulus is the slope of the straight line portion of a stress-strain diagram. Tangent modulus of elasticity is the slope of the stress-strain diagram at any point. Modulus used alone generally refers to tensile modulus of elasticity (or modulus of elasticity in tension). Moduli of elasticity in tension and modulus of elasticity in compressive are approximately equal and are known as Young's modulus.

II. Methods for Repairing or Augmenting Tissue

Methods for repairing and augmenting tissues are described herein. The method includes administering, preferably by injection (e.g., using a syringe or catheter), a biocompatible, biodegradable polymer composition. In one embodiment, the polymers, copolymers, or blends thereof are liquids or pastes at room temperature, wherein upon contact with physiological fluids, the viscosity of the polymer increases to form a solid or semisolid implant suitable for tissue repair and/or regeneration. In another embodiment, the polymer composition contains particles containing a stereocomplex. The particulate compositions is typically in the form of particles which are administered as a suspension or dispersion in a pharmaceutically acceptable solvent.

A. Polymer Compositions

1. Liquid and Pasty Polymer Compositions

In one embodiment, the polyester composition is a liquid or paste at room temperature, wherein upon contact with physiological fluids, the viscosity of the polymer increases to form a solid or semisolid implant suitable for tissue repair and/or augmentation. The polymer may be a homopolymer, copolymer, terpolymer, or blends thereof. In one embodiment, the polymer composition contains a liquid or pasty polyester, copolyester, or blends thereof. In another embodiment, the polymer composition contains a liquid or pasty poly(ester anhydride). In still another embodiment, the polymer composition contains a blend of a liquid and/or pasty polyesters and poly(ester anhydrides).

i. Polyesters

In one embodiment, the polymer composition contains a polyester or copolyester that is a liquid or paste at room temperature. In a preferred embodiment, polyesters include, but are not limited to, hydroxy fatty acid-based polyesters or copolyesters. Suitable hydroxy fatty acids include, but are not limited to, castor oil, vernonia oil and their corresponding fully or partially hydrolyzed or reduced products such as ricinoleic acid, hydroxyl-stearic acid and mono and diglycerides thereof, and esters thereof, hydroxy stearin, and mono and dihydroxy derivatives of unsaturated $C_{18}$ or larger fatty acids, such as oleic acid, linoleic acid, linolenic acid, and arachidonic acid. In a preferred embodiment, the hydroxy fatty acid is ricinoleic acid. The ricinoleic acid-based copolyesters contain one or more comonomers, which are polymerized with ricinoleic acid, to form the copolyesters. In one embodiment, the comonomer is a hydroxy alkanoic acid. Suitable hydroxy alkanoic acids include, but are not limited to, D-lactic acid, L-lactic acid, DL-lactic acid, glycolic acid, 3-hydroxybutyric acid, 4-hydroxybutyric acid, 5-hydroxypentanoic acid, ethylene carbonate, propylene carbonate, and combinations thereof. Liquid or paste copolyesters for drug delivery are described in U.S. Patent Application No. 2007/0036855 to Domb et al. However, the '855 application does not describe methods of using such compositions for soft tissue repair and augmentation. Other classes of monomers that can be incorporated into the polymer include, but are not limited to, alkane dicarboxylic acids, amino acids, diamines, and diols to obtain the desired polymer properties, such as viscosity and degradation rate.

In a preferred embodiment, the polyester is a copolyester formed from ricinoleic acid, castor oil, or vernonia oil and D-lactide, L-lactide, or DL-lactide. The ratio of lactide to hydroxy fatty acid is from about 9:1 to about 5:5. In preferred embodiment, the ratio of lactide to hydroxy fatty acid is 9:1. 8:2, 7:3, 6:4, or 5:5.

Domb et al. describes the synthesis of ricinoleic acid-based copolyesters by ring opening polymerization of ricinoleic lactone (Slivniak, R. and Domb, A. J. "Macrolactones and polyesters from ricinoleic acid", *Biomacromolecules,* 2005, 6, 1679-88; Slivniak, R.; Ezra, A. and Domb, A. J. "Hydrolytic degradation and drug release of ricinoleic acid-lactic acid copolyesters", *Pharm Res.,* 2006, 23, 1306-12). Fatty acids, such as ricinoleic acid, are obtained from natural sources and can be incorporated into biodegradable polymer chains to obtain the desired flexibility, hydrophobicity and injectability.

Ricinoleic acid lactones are typically synthesized using dicyclohexylcarbo-dimide and (dimethylamino)pyridine as catalysts using methodologies well known in the art. Mono- to hexylactones are obtained and polymerized with catalysts commonly used for ring-opening polymerization of lactones, under specific reaction conditions, to form oligomers. Suitable ring-opening catalysts include, but are not limited to, tin octoate, yttrium isopropoxide, trimethylsilanolates, and (2,4-di-tert-butyl-6-{[(2'-dimethylaminoethyl)methylamino]-methyl} phenol)ethylzinc.

Polymers with weight average molecular weights in the range 5000-16000 can be obtained with melting temperatures of 100-130° C. for copolymers containing 10-50% w/w ricinoleic acid residues. The polymers are typically off-white in color and became yellow with an increase in the ricinoleic acid content. The molecular weights of the polymers typically decrease with an increase in the content of the ricinoleic acid lactone.

In another embodiment, the polymer composition contains one or more polyesters or copolyesters containing monomers other than hydroxy fatty acid monomers. Other suitable polyesters include, but are not limited to, poly(e-caprolactone-co-trimethylene carbonate), poly(e-caprolactone-co-p-dioxanone), poly(trimethylene carbonate-co-p-dioxanone), poly (1,4-dioxepan-2-one-co-p-dioxanone), and poly(1,5- dioxepan-2-one-co-p-dioxanone). Other classes of polymers that can be used include, but are not limited to, polyanhydrides and amino acid homopolymers and copolymers with hydroxy acids.

ii. Poly(ester-anhydrides)

In another embodiment, the polymer compositions contain one or more poly(ester anhydrides). Preferred poly(ester-anhydrides) include, but are not limited to, hydroxy fatty acid-based poly(ester-anhydrides). Hydroxy fatty acid-based poly(ester-anhydrides) can be prepared by conversion of a hydroxy fatty acid, such as ricinoleic acid, to a dicarboxylic acid derivative by forming a half ester with an anhydride, such as maleic anhydride or succinic anhydride, which is then polymerized to form prepolymers. The prepolymers are copolymerized with an aliphatic or aromatic polyanhydride, such as sebacic acid, by melt-condensation.

Suitable hydroxy fatty acids include, but are not limited to, castor oil, vernonia oil and their corresponding fully or partially hydrolyzed or reduced products such as ricinoleic acid, hydroxyl-stearic acid and mono and diglycerides thereof, and esters thereof. For example, dicarboxylic acid derivatives of ricinoleic acid and sebacic acid are condensed at low temperature (e.g., 65° C.) to obtain pasty injectable low molecular weight polymers. See Krasko, M. Y., Shikanov, A., Ezra, A., Domb, A. J., Poly(ester anhydride)s prepared by the insertion of ricinoleic acid into poly(sebacic acid), *J. Polym. Sci. Pol. Chem.*, 2003, 41 (8), 1059-1069; Teomim, D.; Nyska, A. and Domb, A. J. "Ricinoleic acid-based biopolymers", *J. Biomed. Mater. Res.* 1999, 45, 258-267. Alternatively, the hydroxy fatty acid is inserted into a preformed polyanhydride polymer chain, for example, by transesterification of a polyanhydride with a hydroxy fatty acid. Upon addition of the liquid polymer to water, the polymer solidifies to form a stable semisolid.

The prepolymers can also be polymerized with a variety of other polyfunctional organic molecules to form other poly(ester-anhydrides) or poly(amide-anhydrides). Suitable polyfunctional organic molecules include, but are not limited to, alkane dicarboxylic acids, amino acids, hydroxy alkanoic acids, lactones, and combinations thereof. Examples of hydroxy alkanoic acid and lactones include, but are not limited to, lactide (L-lactide, D-lactide, or D,L-lactide repeating units), p-dioxanone, glycolide, ε-caprolactone, hydroxybutyric acid, hydroxycaproic acid, trimethylene carbonate, ether lactone repeating units, such as 1,4-dioxepan-2-one and 1,5-dioxepan-2-one, and combinations thereof. Examples of amino acids include, but are not limited to, natural amino acids, such as glycine, alanine, leucine and phenyl alanine, and non-natural amino acids. Examples of dicarboxylic acids include, but are not limited to, linear alkane dicarboxylic acids, such as malonic acid, succinic acid, glutaric acid, pimelic acid, suberic acid, adipic acid, uberic acid, sebacic acid, azelaic acid and decanedioic acid; and linear unsaturated (alkene) dicarboxylic acids, such as fumaric acid, itaconic acid, and maleic acid. Polycarboxylic acids can also be used. Examples of polycarboxylic acid monomers include, but are not limited to, citric acid, dimer or trimer oleic acid, dimer or trimer erucic acid, tartaric acid, malic acid, and polyacrylic acid derivatives.

Other suitable polyfunctional organic molecules include, but are not limited to, ethylene glycol and propylene glycol, with hydroxyl and carboxylic acid terminals; poly(ethylene glycol), poly(propylene glycol), and poly(ethylene-co-propylene glycol) with terminals selected from amino, hydroxyl and carboxylic acid; and polyols, such as pentaeritrithol, propantriol, mucic acid, tartaric acid, and hexahydroxycyclohexane. The synthesis and purification of hydroxy fatty acid-based poly(ester anhydrides), and the use of such materials for drug delivery, is described in U.S. Patent Applications Nos. 2004/0057970 and 2004/0161464 to Domb.

In a preferred embodiment, the composition contains one or more copolymers containing a first monomer derived from a hydroxy fatty acid including, but not limited to, castor oil, vernonia oil and their corresponding fully or partially hydrolyzed or reduced products such as ricinoleic acid, hydroxyl-stearic acid; and mono and diglycerides thereof, and a second monomer derived from a polyfunctional organic molecule, such as D-, L-, or DL-lactide, or a dicarboxylic acid, such as sebacic acid. In a preferred embodiment, the polymer is poly(D-lactide-co-castor oil), poly(L-lactide-co-castor oil), poly(DL-lactide-co-castor oil), and poly(sebacic-co-ricinoleic acid) (PRASA), poly(caprolactone-castor oil), (PCLCO), or blends thereof. The ratio of hydroxy alkanoic acid or diacid to the hydroxyfatty acid is from about 1:1 to about 1:9. In a preferred embodiment, the ratio is 1:1 or 3:7.

2. Particulate Polymer Compositions

In another embodiment, the polymer composition is in particulate form. The particles are suspended or dispersed in a pharmaceutically acceptable solvent and administered by injection, for example via a syringe or catheter. The size of the particles is sufficiently small so that the particle can be expelled from a syringe or catheter needle. In one embodiment, the diameter of the particles is from about 0.5 to about 10 microns, more preferably from 0.5 to 2 microns.

i. Stereocomplexes

In one embodiment, the particulate polymer composition contains one or more stereocomplexes in the form of nano- and/or microparticles. In a preferred embodiment, the stereocomplex is formed from homopolymers or copolymers containing stereoregular segments of D-lactic acid or L-lactic acid or a polypeptide. The stereoregular segments typically contain at least about 10 lactide monomer units. However, for stereoregular segments or blocks other than lactide, the segment or block typically contains at least about 5 monomer units, preferably at least about 10 monomer units. Upon mixing, the complementary segments interact to form a stereocomplex and precipitate from solution as particles. In one embodiment, the polymers are block copolymers containing a stereospecific block of polylactide and one or more blocks including, but not limited to, polycaprolactone, polyglycolide, polytrimethylene carbonate, and polyhydroxybutyrate. Alternatively, the polymer composition can contain a single block copolymer containing segments of both D-PLA and L-PLA. The stereospecific segments interact to form a stereocomplex, which precipitates from solution to form particles. The relative ratios of the stereoregular segments will determine the strength of the complex, the particle size, the degradation time of the complex, and the formation process and yield of particle formation.

Methods for forming stereocomplexes are well known in the art. Stereocomplexes can be prepared by various methods including, but not limited to, mixing of solutions of the individual polymers and precipitation by adding a solution of the two or more complementary stereoselective polymers to a non-solvent or adding the non-solvent to the solution of the polymers. Solutions of PLA based polymers can be prepared in acetonitrile, dichloromethane, chloroform, ethyl acetate, butyl acetate, acetone and tetrahydrofuran (THF). These solutions can be added to a non-solvent such as hexanes, petroleum ethers and ethers. It is preferred to use concentrated polymer solutions and to add the solutions to excess cold (e.g., about 10° C.) non-solvent with high speed mixing. Alternatively, the polymer solution can be sprayed into the non-solvent to form particles where the particles size is affected by the spray condition.

For example, complexation of D-PLA and L-PLA was shown to take place immediately when the polymers were forced to precipitate either by the addition of a non-solvent or by liquid nitrogen. In a typical experiment to generate 5% complexes, D-PLA (19 mg) dissolved in 1 ml dichloromethane (DCM) is mixed with an equal amount of L-PLA in 1 ml DCM. The mixture is thoroughly mixed by vortex for 15 seconds. The solution is transferred to a syringe equipped with a regular sprayer and sprayed into a bath containing 100 ml frozen petroleum ether and liquid nitrogen. The mixture was slowly warmed to −5° C. As the petroleum ether melted, the DCM was extracted from the particles. The particles were dried under vacuum over a drying agent, such as phosphorous pentoxide ($P_2O_5$). The molecular weight of L-PLA was 120 kDa and D-PLA had the following molecular weights: 3 kDa, 10 kDa and 120 kDa. Uniform particle size was obtained ranging from 0.5 to 3 microns depending on the starting molecular weight of the polymers and the reaction conditions for stereocomplexation.

The particles formed typically a uniform particle size. The precipitation conditions generally determine the particle size. However, changes in polymer concentration, mixing rate/speed, and/or changes in the temperature of the solutions/non-solvent, may also affect the particle size. As discussed above, the particles typically have a diameter from about 0.5 to 3 microns. The particles may be prepared having diameters in this range or the particles may be modified after formation of the stereocomplex to achieve the desired diameter. Suitable procedures for modifying the particle size including mechanical procedures, such as milling. Alternative, the particle size can be manipulated by adding the polymer particles to a solution of a stereoregular polymer and allowing the stereocomplex to decomplex and recomplex resulting in different particle compositions, shapes, and/or sizes. If block copolymers are used for stereocomplexation, the polymer structure will have an effect on the particle size and shape as well as on the degradation profile of the resulting stereocomplex.

There are several advantages to particles prepared by stereocomplexation over biodegradable particles made from the same polymers prepared by common micro and nanoparticle preparation. Stereocomplexes of D-PLA and L-PLA are formed spontaneously by mixing the polymer solutions in a common solvent, such as acetonitrile. Uniform particle size is readily obtained, from a few nanometers to microns, and can be controlled through selection of the precipitation solvent, the polymer concentration in the solutions, the ratio of D-PLA and L-PLA (or other stereospecific) segments, the polymer molecular weight, additives added to the stereocomplexation solution, and combinations thereof. Further, the degradation profile of the stereocomplex is different than the degradation profile of the individual polymers used to form the stereocomplex.

3. Properties of the Polymer Compositions

The liquid polymers described herein are characterized by being liquids at room temperature (e.g., 25° C.) in the absence of solvents. The polymers have an inherent viscosity ranging from about 0.05 dL/g to about 0.5 dL/g, preferably from about 0.05 dL/g to about 0.3 dL/g, and most preferably from 0.1 dL/g to 0.2 dL/g as determined in a 0.10 g/dL solution of hexafluoroisopropanol (HFIP) at 25° C. A liquid polymer with an inherent viscosity below 0.05 dL/g may be slightly soluble in body fluids, and a liquid polymer with an inherent viscosity above 0.5 dL/g may be too viscous to be easily injected. The viscosity of the polymers may also vary depending on the molecular weights of the polymers as well as on the chemical composition of the polymers. Generally, the viscosity of the polymers is less than 10,000 poise, preferably in the range from about 20 poise to about 2,000 poise as determined by capillary rheometry. Upon coming in contact with physiological fluids, the viscosity of the polymer increases, resulting in the formation of a semisolid or solid material. In one embodiment, the viscosity of the material increases at least two fold.

While the stereocomplexes are administered in particular form as a suspension or dispersion in a pharmaceutically acceptable solvent, it is possible that upon interaction with tissue and/or physiological fluids, the particles undergo a phase change or transition resulting in a change in the physical and/or mechanical properties of the stereocomplexes. The initial viscosity of the polymer suspension prior to administration is dependent on the concentration of particles in the suspension. In one embodiment, the size and concentration of the particles are selected so that the suspensions can be administered through a small gauge needle (e.g., 27-30 gauge). Once administered, the viscosity of the suspension may change as the suspension medium is absorbed by the tissue.

The polymers compositions should be stable during storage and should degrade at a pre-determined time period from about three weeks to three years, preferably from about three weeks to about two years, and fully eliminated from the body, without causing adverse side effects. In a preferred embodiment, the compositions degrade in vivo over a period of about 18 months. In one embodiment, the polymer composition is administered as a dermal filler that maintains a semisolid or solid state over approximately 1 month prior to degradation and dissolvement. In another embodiment, the polymer compositions is administered as filler that maintains a semisolid or solid state for a period of 6 to 24 months.

The properties of the polymer, particularly the degradation profile and the mechanical properties of the polymer, can be manipulated through selection of the monomers used to prepare the polymers, selection of the polymer molecular weight, incorporation of additives, which alter the porosity of the polymer, additives which alter the mechanical properties of the polymers, and combinations thereof. The mechanical properties of the polymers, such as ultimate compressive strength, stiffness, stress, strain, elongation to break, and Young's modulus E, may be varied/modified depending on the soft tissue to be augmented or repaired. These parameters are dependent on several factors including, but not limited to, the chemical composition of the polymers, the molecular weight of the polymers, additives that are incorporated into and the polymers, and combinations thereof.

The degradation profile and/or mechanical properties of the polymer can also be controlled by the application of external stimuli, such as ultrasound, local heating by radio frequency (RF) or light, iontophoresis, electrical current, and combinations thereof.

4. Active Agents

The polymer compositions described herein may further contain one or more therapeutic agents, prophylactic agents, diagnostic agents, and combinations thereof. Suitable classes of active agents include, but are not limited to, anti-inflammatory agents; local anesthetics; analgesics; antibiotics; growth factors and agents that induce and/or enhance growth of tissue within the filled cavity or control the growth of a certain type of tissue, such as certain types of collagen, and combinations thereof. Exemplary local anesthetics include, but are not limited to, lidocaine and bupivacaine. Exemplary anti-inflammatory agents include, but are not limited to, triamcinolone, dexamethasone, ibuprofen, and indomethacin. Exemplary antibiotics include, but are not limited to, gentamicin and tobramicin. The concentration of the active agent is typically from about 0.1% to about 50% by weight of the composition, preferably from about 0.1% to about 20% by weight of the composition, most preferably from about 1% to about 20% by weight of the composition.

The composition can also contain radiopaque agents in order to track the performance of application and to instantaneously detect potential leakage. The radiopaque agents can be of organic or inorganic nature. In a preferred embodiment, barium sulfate ($BaSO_4$) is used as radiopaque X-ray contrast agent, preferably in a range of between 4 weight % to 30 weight % of the weight of the total composition, preferably in a range of between 5 to 20 weight %, and even more preferably in a range of between 6 to 10 weight %. Preferably the $BaSO_4$ has a specific surface area of greater than or equal to 25 $m^2/g$ and a particle size (diameter) of less than or equal to 100 μm ($d_{50}$). In another preferred embodiment, zirconium oxide ($ZrO_2$) is used as the X-ray contrast agent. The applicable weight percentages are in the same ranges as for $BaSO_4$.

Whereas the addition of radiopaque agents of a particle size of less than or equal to 100 μm average diameter in an amount of between 5 to 30 weight % of the weight of the total composition gives a uniform radiopaque background under X-ray radiation, the addition of few radiopaque particles of an average diameter of about 250 to 600 μm in addition to the uniform radiopaque background allow detection of not only the injection front, but also the injection behavior within the bulk material. This is known as dynamic imaging. This can serve as a further tool for guaranteeing the instantaneous detection of leakage. In a preferred embodiment, radiopaque particles with an average diameter of about 250 to 600 μm, preferably 500 μm are added to the biomaterial. A preferred particle material is gold or titanium.

5. Additives and Excipients

The polymer compositions may also contain one or more pharmaceutically acceptable additives or excipients. The additives may modify or affect one or more of the physical and/or mechanical properties of the polymer compositions. For example, the polymer compositions may contain nanoparticles and microparticles prepared from or containing biodegradable polymers, ceramics, absorbable inorganics, and combinations thereof for better control of tissue filling and duration. Such particulate phases may also contain particles loaded with an active agent that provide a controlled release of the agent or agents over a desired time period. Lipid based particles and vesicles, such as lipospheres and liposomes may be added to the composition to increase consistency and dispersibility. In embodiments where the polymer composition is a particulate, additives which help to disperse the polymer in the pharmaceutically acceptable solvent, such as surfactants and dispersing agents, may be added. Suitable surfactants include, but are not limited to, Tweens®, Spans®, poly(ethylene glycol), poly(ethylene glycol-co-propylene glycol), phospholipids, and combinations thereof. The particulate compositions may also contain isotonicity modifying agents, pH modifying agents, thickening agents, and combinations thereof.

The concentration of the additives and excipients is typically from about 1% to about 50% by weight of the composition, preferably from about 1% to about 30% by weight of the compositions, more preferably from about 1% to about 20% by weight of the composition.

Apart from their function as X-ray contrast agents, silica, zirconium oxide and barium sulfate can also serve as fillers in the composition. The addition of fillers can result in an increase of the mechanical properties (ultimate compressive strength and Young's modulus E) of the materials.

IV. Methods of Administration

The polymer compositions can be administered with a syringe and needle or a variety of devices, such as catheters: "Needle", as used herein, refers to devices that can be used to administer, deliver, inject, or otherwise introduce the polymer compositions to a subject for tissue repair and/or augmentation. Thus, as defined herein, needle includes needle, all needle-like devices, and all other annular introduction devices, such as tubing, etc. Specific examples include needles, hypodermic needles, surgical needles, infusion needles, catheters, trocars, cannulas, tubes, and tubing used for clinical, surgical, medical, procedural, or medical purposes. In one embodiment, the polymer composition is administered by injection, for example, via a syringe. For deep implantation in the body, the syringe may be connected to a tube or catheter fitted to the outlet for administering the liquid polymers into a site within the body. An automated injector may be used for better control of the injection of the polymer formulations Other delivery devices have been developed and described in the art to administer viscous liquids, such as the carpule devices described in U.S. Pat. Nos. 4,664,655 and 4,758,234 to Orentriech. Additionally, to make delivery of the polymer compositions as easy as possible for doctors, a leveraged injection ratchet mechanism or powered deliver mechanism may be used. In one embodiment, the polymers are preloaded in a cylindrical container or cartridge having two ends. The first end would be adapted to receive a plunger and would have a movable seal placed therein. The second end or outlet would be covered by a removable seal and be adapted to fit into a needle housing to allow the polymer composition in the container to exit the outlet and enter a needle or other hollow tubular member of the administration device.

In the embodiments where the polymer is a liquid at room temperature, the polymer may be administered neat (i.e., without solvent) or in combination with a pharmaceutically acceptable solvent. For pasty polymers, a water-miscible, pharmaceutically acceptable solvent may be added to decrease the viscosity of the polymer and improve the injectability of the polymer. Suitable solvents include, but are not limited to, glycerol, polyethylene glycol, N-methyl pyrrolidone, dipropylene glycol and ethyl lactate. For particulate polymers, the polymers are typically suspended or dispersed in a pharmaceutically acceptable solvent, such as water or saline solution.

The compositions may contain one or more pharmaceutically acceptable excipients including, but not limited to, surfactants, dispersing agents, pH modifying agents, viscosity modifying agents, thickening agents, isotonicity modifying agents, and combinations thereof.

V. Kits

Kits containing the polymer compositions are described. Part of the kit can be a sterile container containing the polymer composition and optionally one or more additives or excipients. The polymer composition may be neat (e.g., free of solvent) or the polymer composition may be dissolved or dispersed in a pharmaceutically solvent. In some embodiments, the kit may contain a second sterile container containing the pharmaceutically acceptable solvent for dissolving or dispersing the polymer composition. In these embodiments, the polymer composition can be added to the pharmaceutically acceptable solvent to form a solution or dispersion and then introduced into a device for administration. The polymer composition and/or the pharmaceutically acceptable solvent may contain one or more pharmaceutically acceptable additives or excipients.

In some embodiments, the kit may contain a device or devices for administering the polymer composition. In one embodiment, the device would have an outlet for the polymer composition, an ejector for expelling the composition and a hollow tubular member fitted to the outlet for administering the polymer composition into an animal. For example, the kit may contain a syringe loaded with the polymer composition, wherein the syringe has a fixation point (i.e., a luar lock) for a needle and a set of needles with various gauges suitable for various applications. The kit may also contain instructions for how to administer the compositions.

VI. Methods of Use

The injectable polymer compositions can be used for a variety of soft tissue repair and augmentation procedures in a subject, preferably a mammal, such as humans, dogs, cats, horses, pigs, cows, and sheep. For example, the injectable polymer compositions can be used in facial tissue repair or augmentation, including, but not limited to, camouflaging scars, filling depressions, smoothing out irregularity, correcting asymmetry in facial hemiatrophy, second branchial arch syndrome, facial lipodystrophy and camouflaging age-related wrinkles as well as augmenting facial eminences (lips, brow, etc.). Additionally, the injectable polymer compositions can be used to restore or improve sphincter function such as for treating stress urinary incontinence. Other uses of the injectable polymer compositions may also include the treatment of vesicoureteral reflux (incomplete function of the inlet of the ureter in children) by subureteric injection and the application of these liquid polymers as general purpose fillers in the human body.

Surgical applications for the injectable polymers compositions include, but are not limited to, facial contouring (e.g., frown or glabellar line, acne scars, cheek depressions, vertical or perioral lip lines, marionette lines or oral commissures, worry or forehead lines, crow's feet or periorbital lines, deep smile lines or nasolabial folds, smile lines, facial scars, lips and the like); periurethral injection including injection into the submucosa of the urethra, along the urethra, and at or around the urethral-bladder junction to the external sphincter; ureteral injection for the prevention of urinary reflux; injection into the tissues of the gastrointestinal tract for the bulking of tissue to prevent reflux; to aid in sphincter muscle coaptation, internal or external, and for coaptation of an enlarged lumen; intraocular injection for the replacement of vitreous fluid or maintenance of intraocular pressure for retinal detachment; injection into anatomical ducts to temporarily plug the outlet to prevent reflux or infection propagation; larynx rehabilitation after surgery or atrophy; and any other soft tissue which can be augmented for cosmetic or therapeutic affect.

The concentration of the polymer(s) in the composition can be readily determined by the attending physician based on the indication; height, weight, and/or age of the patient; and the period of time the material needs to be in place. The concentration of the polymer(s) in the composition is from about 20% to about 100% by weight of the composition.

EXAMPLES

Example 1

Synthesis of Vernonia Oil Based Polyesters

Vernonia oil (Ver-Tech, Inc., Bethesda, Md.) containing an average of 2.1 epoxy functionalities per molecule was used in this study.

Opening of Epoxy Group

The reaction was conducted using a single neck reaction vessel equipped with a mechanical stirrer and heated using an oil bath. Vernonia oil has an average of 2.1 epoxy groups per molecule. The lactic acid was calculated at a 1:1 molar ratio to the epoxy groups. The reaction mixture was heated to 120° C. and reaction was stirred for 12 h. The reaction was monitored by NMR and IR to confirm the disappearance of the epoxy groups.

Polymer Synthesis by Polycondensation

The polyesters were synthesized using a single neck reaction vessel equipped with a mechanical stirrer and heated using an oil bath. Modified vernonia oil and lactic acid were added into the vessel with different weight/weight ratios (lactic acid used for the ring opening step was included in the total lactic acid calculation). The catalyst, $H_3PO_4$ (0.5% w/w), was added to the reaction mixture prior to polymerization. During esterification, the temperature was slowly increased to 180° C. and the mixture was stirred for different time periods under constant $N_2$ flow. The resulting polymers were evaluated by GPC and NMR.

Polymer Synthesis by Ring Opening Polymerization

The polyesters were synthesized using a single neck reaction vessel equipped with a mechanical stirrer and heated using an oil bath. Modified vernonia oil and lactide were added into the vessel with different weight/weight ratios (lactic acid used for the ring opening was included in the total lactic acid calculation). The reaction was conducted for 5 h at 140° C.

Biodegradable copolyesters of lactic acid and vernonia oil having a 60:40 w/w of lactide to vernonia oil ratio were synthesized by thermal polycondensation or ring opening polymerization to yield liquid-viscous materials (Scheme 1). The opening of the epoxy ring was performed using lactic acid. The hydroxyl groups of lactic acid react with the epoxy group under mild conditions. The epoxy groups were completely reacted after 8 h, as confirmed by NMR an IR.

Scheme 1: Synthesis of poly(lactic acid-co-vernonia oil) polyesters

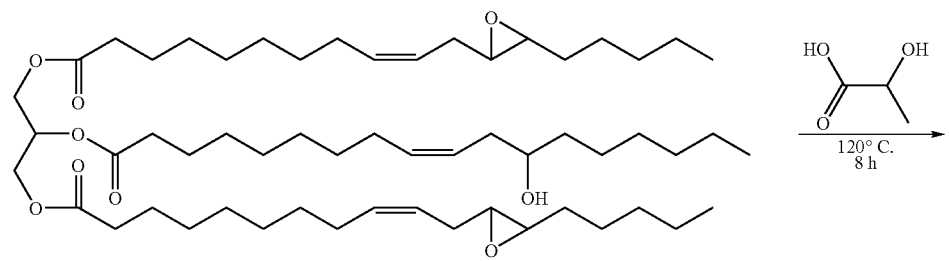

-continued

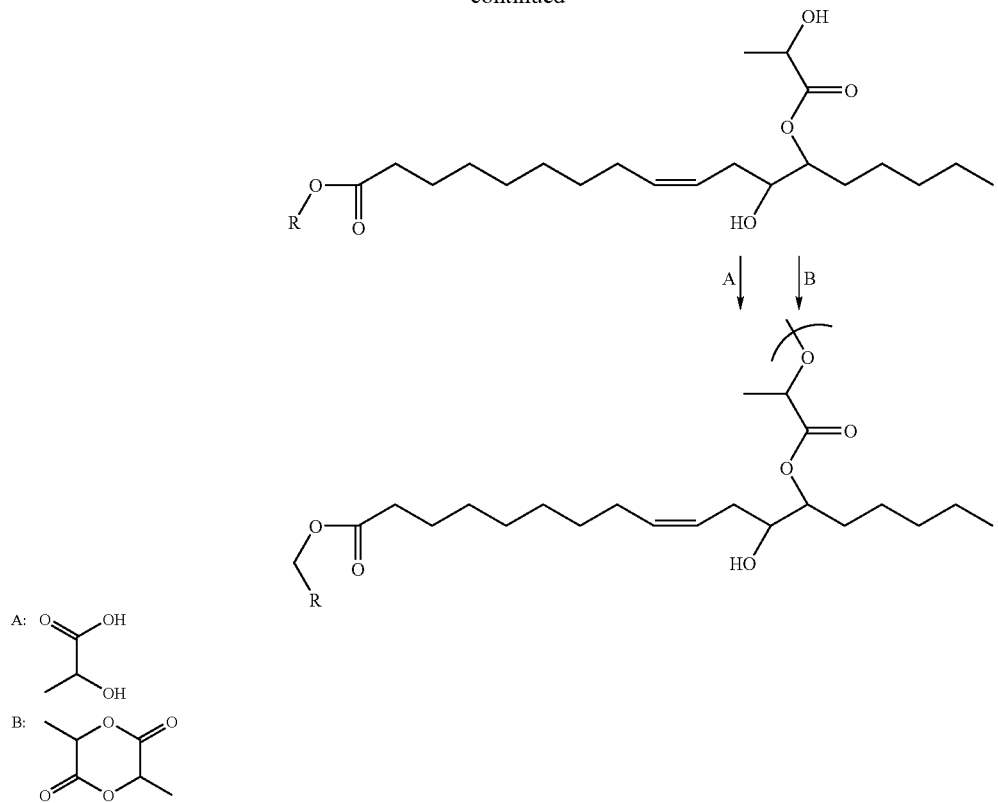

Polymerization by Polycondensation

Polymerization was continued for 7 h. The resulting polymers, however, had high molecular weights and were not injectable at room temperature. The polymerization time was reduced to 4 h; however, the resulting molecular weights were still too high. Polymerization time was reduced to 1.5 h. The molecular weights were considerably lower resulting in polymers that were liquids or pastes at room temperature and thus should be injectable (see Table 1).

Example 2

Synthesis and Characterization of Injectable Castor Oil Based Polyesters

Materials

Castor oil was purchased from Floris (Israel). Ricinoleic acid (98% pure) was prepared by hydrolysis of castor oil and further purified by extraction with an aqueous solution, for

TABLE 1

Polymers Synthesized by Polycondensation and Ring Opening Polymerization

| Lactic acid conformation | Polycondensation | | | | | | Ring opening polymerization | |
|---|---|---|---|---|---|---|---|---|
| | 1.5 h | | 4 h | | 7 h | | 5 h | |
| | Mn/Mw | appearance | Mn/Mw | appearance | Mn/Mw | appearance | Mn/Mw | appearance |
| L | Mn = 2200 | Liquid | Mn = 3300 | Viscous Liquid | Mn = 4500 | Viscous Liquid | Mn = 3200 | Solid brittle |
| | Mw = 2800 | | Mw = 7200 | | Mw = 16000 | | Mw = 6800 | |
| D | Mn = 2150 | Liquid | Mn = 3600 | Viscous Liquid | Mn = 4500 | Viscous Liquid | Mn = 3600 | Solid soft |
| | Mw = 2700 | | Mw = 9250 | | Mw = 16100 | | Mw = 9100 | |
| DL | Mn = 1700 | Liquid | Mn = 3730 | Viscous Liquid | Mn = 5100 | Viscous Liquid | Mn = 3470 | Liquid |
| | Mw = 2700 | | Mw = 10150 | | Mw = 20100 | | Mw = 6100 | |

Polymerization by Ring Opening Polymerization

Ring opening polymerization was conducted for 5 h and molecular weights of the polymers were considerably lower compared to polymers synthesized by polycondensation (see Table 1 above).

example sodium chloride solution or carbonate solution, to remove hydrophilic contaminants. L-lactic acid (L-LA) and DL-lactic acid (DL-LA) were purchased from J. T. Baker (Deventer, The Netherlands). D-lactic acid was prepared from the hydrolysis of D-lactide in water. D-lactide was purchased from Purac Biochem (Gorinchem, The Netherlands). CDCl$_3$, for NMR, was purchased from Sigma-Aldrich (Rehovot, Israel). All solvents and salts were analytical grade from Aldrich or Biolab (Jerusalem, Israel).

Instrumentation

IR spectra were performed on monomer and polymer samples cast on NaCl plates from $CH_2Cl_2$ solutions on Bruker (Vector 22 System FT-IR). UV spectra were taken on a Kontron Instruments Uvicon model 930 (Msscientific, Berlin, Germany).

Thermal analysis was determined on a Mettler TA 4000-DSC differential scanning calorimeter (Mettler-Toledo. Schwerzzenbach, Switzerland), calibrated with Zn and In standards, at a heating rate of 10° C./min under nitrogen atmosphere.

Melting temperatures of the co-polyesters were determined using Fisher Scientific melting point apparatus.

Molecular weights of the co-polyesters were estimated on a gel permeation chromatography (GPC) system consisting of a Waters 1515 Isocratic HPLC Pump, with 2410 Refractive Index detector (RI) (Waters, Mass.), a Rheodyne (Coatati, Calif.) injection valve with a 20 µL loop. Samples were eluted with chloroform through a linear Styrogel column, 500 Å-pore size (Waters, Mass.) at a flow rate of 1 mL/min. The molecular weights were determined relative to polystyrene standards (Polyscience, Warrington, Pa.) with a molecular weight range of 500 to 20,000 Da using BREEZE 3.20 version, copyright 2000 Waters corporation computer program. The hydrolysis was conducted in 0.1 M phosphate buffer (pH 7.4) at 37° C. with a constant shaking of 100 rpm. 1H NMR spectra (in $CDCl_3$) was recorded on a Varian 300 spectrometer using TMS as internal standard (Varian Inc., Palo Alto, Calif.). Optical rotations of polymers were determined by Optical Activity LTD polarimeter (Cambridgeshire, England) in 10 mg/mL polymer in $CHCl_3$ solution.

The viscosity of the polymers was measured using a Brookfield LVDV-III programmable viscometer coupled to a temperature-controlling unit. Cylindrical spindle LV4 was used. Temperature sensitivity tests were performed starting at a temperature of 60° C. and decreased to room temperature (25° C.) by applying constant rotational speed. Detection of rheological behavior was performed by measuring shear stress and/or viscosity at different shear rates, starting at 0.209 $sec^{-1}$, for more viscous polymers and up to 15.7 $sec^{-1}$ for less viscous polymers. All experiments were performed in triplicate.

Synthesis of Castor Oil/Ricinoleic Acid Based Aliphatic Polyesters

All polyesters were synthesized using a single neck reaction vessel equipped with a mechanical stirrer and heated using an oil bath. Lactic acid and ricinoleic acid/castor oil were added into the vessel with different weight/weight ratios. The catalyst, $H_3PO_4$ (0.5% w/w), was added to the reaction mixture prior to polymerization. During esterification, the temperature was slowly increased to 180° C. and the mixture was stirred for 1.5 h under constant $N_2$ flow. The polycondensation was conducted under low vacuum (15 mbar). The reaction continued for additional 24 h. The resulting polymers were evaluated by GPC, IR NMR and melting point. Because of the relatively narrow Mw/Mn distributions (P≤2), no further purification steps were taken.

Results and Discussion

Ricinoleic Acid Based Polyesters

Biodegradable copolyesters of lactic and ricinoleic acids at various w/w ratios from 90:10 to 50:50, were synthesized by thermal polycondensation to yield solid and liquid-viscous materials.

The solid polymers P(LA:RA) 9:1 and 8:2 had an yellowish color and melted at temperatures between 60 and 110° C. The polymers P(LA:RA) 7:3 to 6:4 were extremely viscous liquids. P(LA:CO) 5:5 were viscous liquids at room temperature. Polymers with molecular weights in the range 2000 to 11000 were obtained. All polymers possess typical IR absorption at 1748 cm−1 corresponding to the ester carbonyl stretching bands. $^1$H NMR spectra of the polymers confirmed the chemical composition. (see Table 2).

TABLE 2

Summary of Ricinoleic Acid Based Polyesters

| Lactic/ ricinoleic acid ratio | L Lactic acid | | D Lactic acid | |
|---|---|---|---|---|
| | appearance | Mn/Mw | appearance | Mn/Mw |
| 80:20 | Solid brittle Mp = 110° C. | Mn = 4510 Mn = 10950 | Solid brittle Mp = 98° C. | Mn = 3170 Mw = 6770 |
| 70:30 | Semi solid Mp = 60° C. | Mn = 4120 Mw = 10100 | Semi solid Mp = 55° C. | Mn = 3260 Mw = 7020 |
| 60:40 | Liquid at RT | Mn = 4400 Mw = 10500 | Liquid at RT | Mn = 3500 Mw = 7200 |
| 50:50 | Liquid at RT | Mn = 4200 Mw = 9800 | Liquid at RT | Mn = 2000 Mw = 4000 |

The 80:20 polymer was not injectable. The 70:30 polymer was pasty at room temperature and could be injected by using a larger gauge needle, such as an 19 or 20 gauge needle. However, dilution of the polymer in a pharmaceutically acceptable, water-miscible solvent should decrease the viscosity of the polymer and therefore allow injection through a smaller gauge needle. The 40% ricinoleic acid-containing polymers wee injectable with 27 and 30 gauge needles at room temperature.

Since castor oil has three functional hydroxyl groups on the molecule, the expected polymers should be branched and therefore have lower viscosity and be injectable at room temperature.

Hydrolytic Degradation of Ricinoleic Acid Based Polymers

The hydrolysis of the lactic acid-ricinoleic acid copolyesters was monitored by weight loss of the specimens, and changes in polymer molecular weight. P(LA:RA) prepared by polycondensation from L-lactic acid or D-lactic acid and ricinoleic acid were compared.

L-lactic acid-based polyesters showed a two phase degradation pattern. First, up to about 30 days, the weight loss was minor, followed by a stabilization in sample weight. The hydrophilicity/hydrophobicity of P(L:LA-RA) polymers is dependent on its monomer composition. Also the monomer composition defines the crystallinity of the polymer. P(L:LA:RA) 8:2 is a relatively hydrophilic crystalline polymer, whereas P(L:LA-RA) 7:3 and 6:4 w/w are relatively hydrophobic noncrystalline polymers. Increased crystallinity generally reduces the degradation rate as evidenced by the fact that P(LL:LA:RA) 8:2 showed the slowest degradation rate. Hydrophobicity compensates for loss of crystallinity resulting in a similar sample weight loss for P(L:LA:RA) 7:3 and 6:4. D-lactic acid based polyesters showed minimal change in polymer degradation with an almost zero-order weight loss.

Generally the weight loss of D-lactic acid based polymers was higher then L-lactic acid based polyesters, especially for P(D:LARA) 8:2. It is possible that the crystallinity of this polymer is lower and does not compensate for the relatively hydrophilic nature of the polymer. The most hydrophobic polymer, P(LA:RA) 6:4, showed the slowest degradation rate non dependant of lactic acid conformation.

The molecular weight of the all the polymers decreased to about 2000 Da during 80 days of incubation, regardless of the initial molecular weight and polymer composition. A slight decrease in molecular weight was observed during the first 30 days, followed by a slow degradation phase, which kept the Mn at 2000-1500 for approximately three months.

Castor Oil Based Polymers

Branched copolyesters of lactic acid and castor oil at various w/w ratios from 90:10 to 50:50, were synthesized by thermal polycondensation to yield solid and viscous liquid materials. The degree of polymerization of lactic acid and castor oil was determined by measuring the increase in molecular weight using GPC. The polymerization pattern showed zero-order increase of molecular weight for polyesters with feed ratios of 25% and higher. Polyesters containing 10% of castor oil showed zero order increase in the molecular weight up to 7 hours, followed by a slight increase in the molecular weight. The same pattern was observed for Mn increase. Table 3 summarizes the changes in polymer molecular weight and appearance.

and molecular weight. It is possible to synthesized polymers with higher molecular weights, but these polymers are not injectable at room temperature. To prepare injectable polymers, the molecular weight must be closely monitored and should not exceed the values shown in Table 4. Another option is to increase the castor oil content in the polymer. Increasing the castor oil content in the polymer will also increase the polymer hydrophobicity. Polyesters with castor oil feed ratios are summarized in Table 5.

TABLE 5

P(LA:CO)5:5 Synthesized form Different Lactic Acid Conformations

| Lactic acid conformation | Calculated lactic acid/ castor oil ratio | Mn/Mw | Viscosity at room temperature (cP) |
|---|---|---|---|
| L-lactic acid | 5:5 | Mn = 2600<br>Mw = 3670 | 6900 |

TABLE 3

Changes in Polymer Molecular Weight and Appearance

| Lactic acid/castor oil feed w/w ratio | 3 h Mn/Mw | appearance | 5 Mn/Mw | appearance | 7 Mn/Mw | appearance | 24 h Mn/Mw | appearance | m.p |
|---|---|---|---|---|---|---|---|---|---|
| 90:10 | Mn = 400<br>Mw = 145 | Liquid | Mn = 2900<br>Mw = 3300 | Liquid | Mn = 2800<br>Mw = 4300 | Solid | Mn = 4300<br>Mw = 6800 | Solid brittle | 115° C. |
| 80:20 | Mn = 980<br>Mw = 2000 | Liquid | Mn = 3050<br>Mw = 3700 | Liquid | Mn = 3750<br>Mw = 5200 | Solid | Mn = 6950<br>Mw = 14000 | Solid soft | 75° C. |
| 70:30 | Mn = 2300<br>Mw = 2550 | Liquid | Mn = 2700<br>Mw = 3150 | Liquid | Mn = 3150<br>Mw = 4100 | Liquid | Mn = 6600<br>Mw = 10600 | Liquid | Liquid at R.T |

The polymers P(LA:CO) 9:1 and P(LA:CO) 8:2 are solids at room temperature after 7 hours of polymerization, reaching Mw values of 4300 and 5200 respectively. After 24 h of polymerization, the polymers showed Mw values of 6800 (P(LA:CO)9:1) and 14000 (P(LA:CO)8:2). The solid polymers P(LA:CO) 9:1 and 8:2 had a yellowish color and melted at temperatures between 45° C. and 75° C. The polymer P(LA:CO) 7:3 was an extremely viscous liquid. The aim of the study was to prepare polymers injectable at room temperature. The polymers containing 30% of castor oil were not injectable, therefore the castor oil ratio was increased to 40 and 50%. Different conformations of lactic acid (L/D/DL) were also used. The properties of the P(LA:CO)6:4 polymers are summarized in Table 4.

TABLE 4

P(LA:CO)6:4 Synthesized form Different Lactic Acid Conformations

| Lactic acid conformation | Calculated lactic acid/castor oil ratio | Mn/Mw | Viscosity at room temperature (cP) |
|---|---|---|---|
| L-lactic acid | 6:4 | Mn = 2600<br>Mw = 3670 | 72200 |
| D-Lactic acid | 6:4 | Mn = 2900<br>Mw = 4100 | 47500 |
| DL-Lactic acid | 6:4 | Mn = 2800<br>Mw = 3800 | 37300 |

The P(LA:CO) 6:4 copolymers were viscous liquids at room temperature. The viscosity of the polymer, and thus its injectability, was dependent on the lactic acid conformation TABLE 5-continued P(LA:CO)5:5 Synthesized form Different Lactic Acid Conformations

| Lactic acid conformation | Calculated lactic acid/ castor oil ratio | Mn/Mw | Viscosity at room temperature (cP) |
|---|---|---|---|
| D-Lactic acid | 5:5 | Mn = 2900<br>Mw = 4100 | 12600 |
| DL-Lactic acid | 5:5 | Mn = 2800<br>Mw = 3800 | 9400 |

All the polymers possessed the typical IR absorption at 1748 $cm^{-1}$ corresponding to the ester carbonyl stretching bands. 1H NMR spectra of the polymers confirmed their composition.

Polymer Viscosity and Injectability

The viscosity of the polymers is an important characteristic, since the viscosity of bulk polymer correlates to polymer injectability. Determination of viscosity threshold under which the polymer is still injectable allows easy and repeatable evaluation of injectability. One of the factors that can have an effect on the rheological behavior of a material is temperature. Some materials are quite sensitive to temperature, and relatively small variations in temperature can result in significant changes in viscosity. Measuring viscosity at different shear rates is also important when a material is to be subjected to a variety of shear rates in processing (preparation of polymer loaded with drug by trituration) or use (injecting of the polymer via a needle or catheter).

Figure 2:
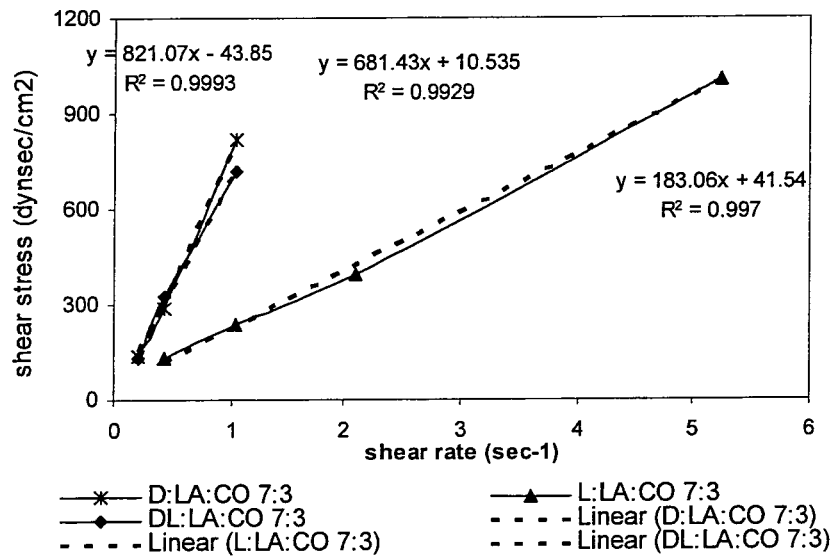
FIG. 2 is a graph showing the shear rate-shear stress relationship at room temperature for various (cP) poly(lactide-co-castor oil) copolymers having a 7:3 ratio of lactide to castor oil. The polymers are poly(D-lactide-co-castor oil) (*), poly(DL-lactide-co-castor oil) (♦), and poly(L-lactide-co-castor oil) (▲).

The viscosity of three sets of polymers was measured; P(LA:CO) 7:3, P(LA:CO) 6:4 and P(LA:CO) 5:5. FIG. 1 shows the viscosities of the three different P(LA:CO)7:3 polymer: poly(D-lactide-co-castor oil) (*), poly(L-lactide-co-castor oil) (♦), and poly(DL-lactide-co-castor oil) (▲). The viscosity of P(LA:CO) 7:3 was measured at three different shear rates (0.209, 0.418, and 1.045 s$^{-1}$). The viscosity was measured starting at 55° C. decreasing to the lowest temperature at which a data point could be measured (32° C. in the case of P(L:LA:CO) 7:3, which had the highest viscosity among the polymers). P(LA:CO) 7:3 show properties of a Newtonian fluid at all temperatures and its viscosity was not affected by shear rate applied. The conformation of the lactide had a direct effect on polymer viscosity, and amorphous polyesters prepared from DL-lactic acid had lowest viscosity of the polymers studied. The polymer behavior is again confirmed by constant shear rate/shear stress correlation (see FIG. 2)

Figure 3:
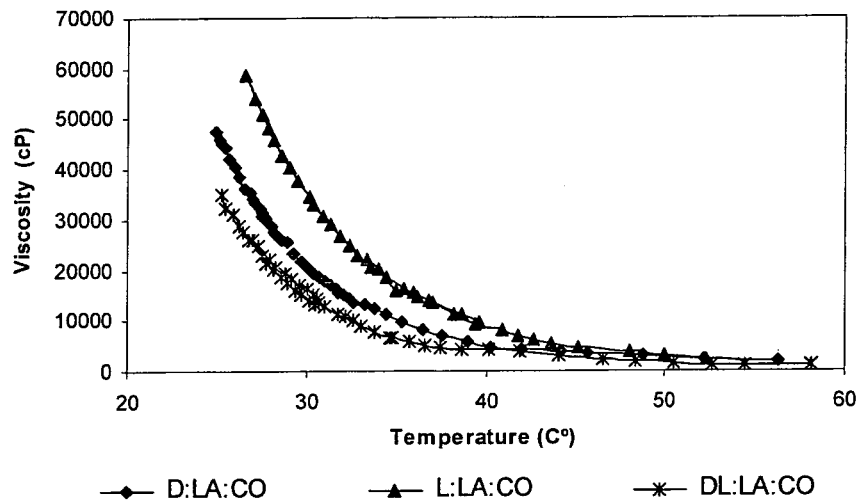
FIG. 3 is a graph showing the viscosity (cP) of three different poly(lactide-co-castor oil) copolymers having a 6:4 ratio of lactide to castor oil versus temperature (° C.) at three different shear rates. The polymers are poly(D-lactide-co-castor oil) (♦), poly(DL-lactide-co-castor oil) (*), and poly (L-lactide-co-castor oil) (▲).

FIG. 3 shows the viscosities of the polymer P(LA:CO) 6:4. The viscosity was measured starting at 60° C. and decreasing to room temperature. The polymers are poly(D-lactide-co-castor oil) (♦), poly(DL-lactide-co-castor oil) (*), and poly (L-lactide-co-castor oil) (▲). P(LA:CO) 6:4 has a much lower viscosity than P(LA:CO)s 7:3 (one-fold decrease) because of its higher castor oil content that contributes to the liquidity of the polymer. P(LA:CO) 6:4 acted as a Newtonian fluid, and its viscosity was not affected by shear rate applied in this range of temperatures. Because of the lower viscosity of the polymer, the viscosity was measured at higher shear rates. At room temperature at all shear rates applied (2 and 5.225 sec$^{-1}$), the viscosity of P(LA:CO)s was about 60000 cP for L-lactide based polyesters, 50000 cP for D-lactide based polyesters, and 40000 cP for DL-lactide based polyesters. Since only P(DL(LA:CO) was easily injectable, the 40000 cP viscosity value can be established as a viscosity threshold value for injectability. The relationship between the shear stress (F) and the shear rate (dv/dr) is expressed mathematically in the Newton equation:

$$F=\eta dv/dr$$

where the proportionality constant, η, is the coefficient of viscosity. es 4 and 5 show the relationships between the shear rate and shear stress of the polymers.

Figure 4:
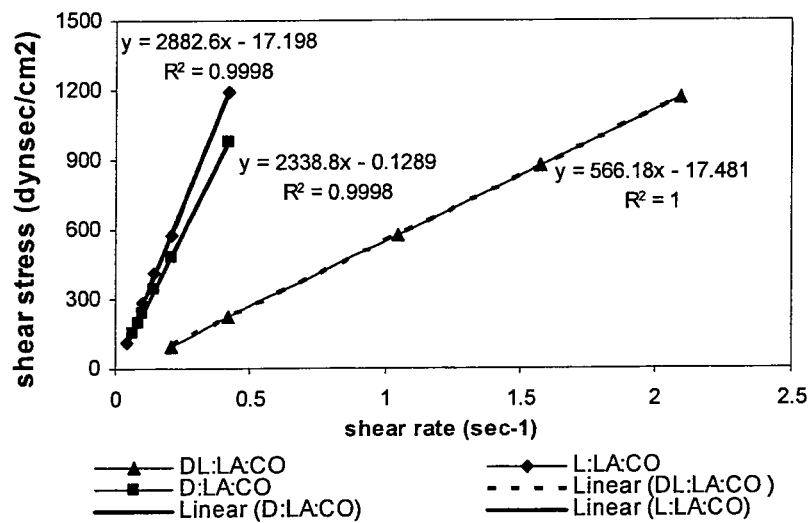
FIG. 4 is a graph showing the shear rate-shear stress relationship at room temperature for various (cP) poly(lactide-co-castor oil) copolymers having a 6:4 ratio of lactide to castor oil. The polymers are poly(D-lactide-co-castor oil) (♦), poly(DL-lactide-co-castor oil) (▲), and poly(L-lactide-co-castor oil) (■).
Figure 5:
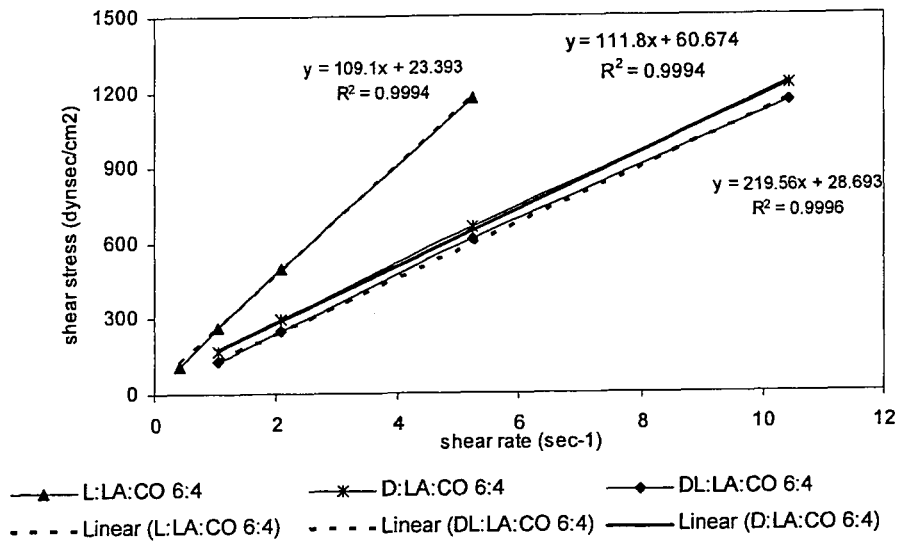
FIG. 5 is a graph showing the shear rate-shear stress relationship at 37° C. for various (cP) poly(lactide-co-castor oil) copolymers having a 6:4 ratio of lactide to castor oil. The polymers are poly(D-lactide-co-castor oil) (*), poly(DL-lactide-co-castor oil) (♦), and poly(L-lactide-co-castor oil) (▲).
Figure 6A:
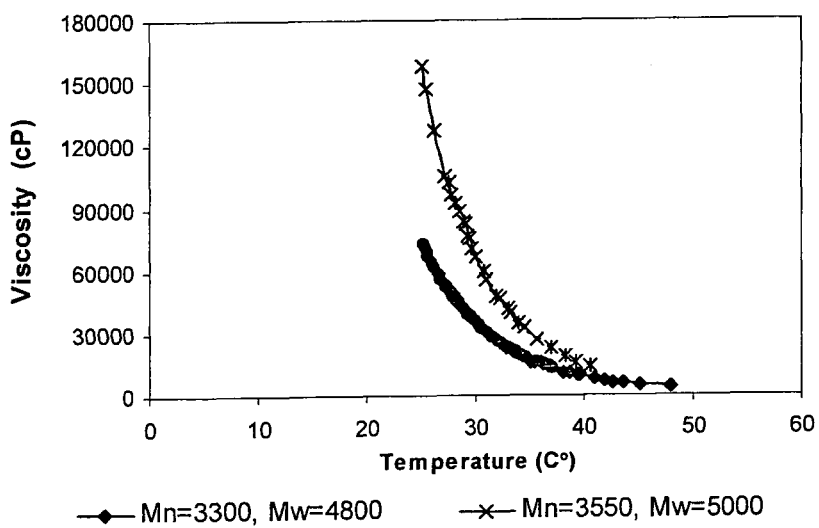
FIGS. 6A-6C are graphs showing the effect of molecular weight on polymer viscosity for L-lactic acid-based polyesters (FIG. 6A), D-lactic acid-based polyesters (FIG. 6B) and DL-lactic acid-based polyesters (FIG. 6C).
Figure 6B:
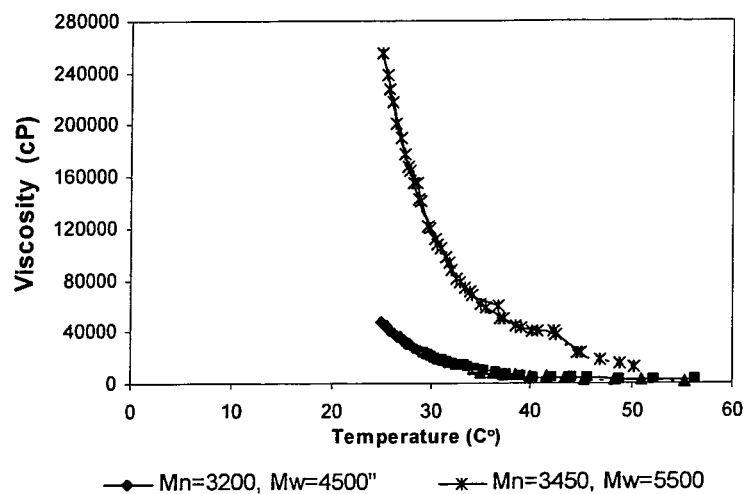
Figure 6C:
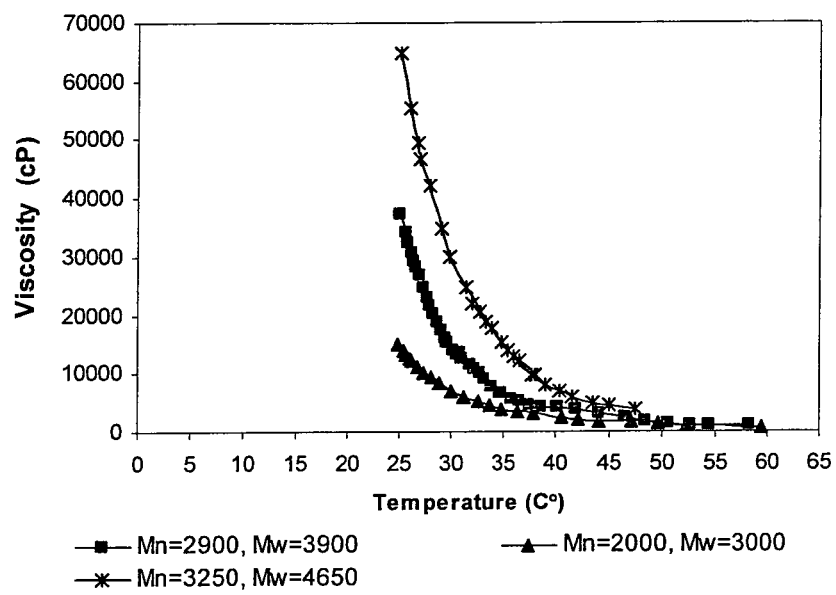

P(LA:CO)s 6:4 behaves as Newtonian fluid showing constant shear rate/shear stress relationship both at room temperature (see FIG. 4) and at 37° C. (see FIG. 5). In most cases, a slight increase in the molecular weight does not affect the viscosity of the polymers. However, this was not observed with P(LA:CO) 6:4. FIGS. 6a-c show that slight increases in molecular weight result in a significant increase in viscosity, and the polymers are non-injectable at room temperature and standard pressure. The viscosity of P(LA:CO) 5:5 is much lower than the viscosity of P(LA:CO) 6:4. It was possible to measure the viscosity of these polymers at higher shear rates (up to 10 sec$^{-1}$ at room temperature).

Hydrolytic Degradation of Castor Oil Based Polyesters

The hydrolysis of the copolyesters was monitored by weight loss of the specimens, and changes in polymer molecular weight. P(LA:CO) prepared by polycondensation from L/D or DL-lactic acid and castor oil with a feed ratio of 60:40 were compared. Lactic acid based polyesters showed almost zero-order decrease in molecular weight. Generally two factors affect the degradation: hydrophilicity/hydrophobicity and crystallinity of the polymer. P(LA:CO) 6:4 is a relatively hydrophobic noncrystalline polymer.

The number average molecular weight (Mn) loss was monitored by GPC. The Mn decreased to about 2000 Da during 100 days of incubation, regardless of the initial molecular weight and polymer composition. During the first 40 days of incubation, the molecular weight remained almost constant.

Example 3

Biocompatibility, Biodegradation and Elimination of p(SA:RA) 3:7 in Rats

Objective

The goal of this study was to examine the systemic and local effects of biodegradable poly(ester-co-anhydrides) and polyesters implanted in rats for a period of 6 weeks and to examine the degradation behavior of the polymer matrix from the implantation site.

Methods

The following polymers were chosen for the study: poly (sebacic-co-ricinoleic acid) 3:7 (PRASA), poly(caprolactone-castor oil) 1:1 (PCLCO) and poly(lactic acid-castor oil) 1:1 (PLACO). All polymers were easily injectable through a 27 gauge needle. The polymers were synthesized by melt condensation and had a weight average molecular weight (Mw) of 4,000.

Animals: Female Spraque-Dawley (SD) rats were obtained from Harlan Laboratories (Jerusalem, Israel). The rats' weight at implantation was 210±15.0 g. The rats were housed in the SPF unit of the animal facility and were allowed free access to food and water. The rats were randomly assigned to three groups (n=4): a control group, Group A, consisting of rats which received saline at the same injection-implantation sites and were anesthetized in the same way as group received polymer implantation, and Groups B, C, and D consisting of rats implanted with PRASA, PCLCO, and PLACO, respectively.

Implantation

Each rat was removed from its respective cage and anesthetized using isotonic 5% chloral hydrate solution (0.64 ml/100 g) administrated through the intraperitonal route. Each rat had been shaved using an animal clipper on both dorsum sides and the femoral areas. The animals were prepared aseptically using 70% alcohol. The polymer implants were injected through a 22 G needle subcutaneously on both sides of each animal and intramuscularly into the femoral muscle on both sides. The rats were allowed to wake-up in the operating room before they were returned to their cages. Samples of 0.2 ml were injected subcutaneously unless otherwise indicated.

Clinical Chemistry and Hematology Measurements

At 5 days pre-implantation and the day of implantation, blood samples were drawn from the tail vein for determination of the baseline parameters for each rat. At 3, 7, 21 and 42 days post-implantation, the rats were anesthetized and blood samples were drawn by cardiac punctuation. The samples were then analyzed for clinical chemistry and hematological parameters for each rat.

Histological Evaluations of Organ Sites and Implant Sites

At the 3, 7, 21 and 42 days post-implantation, the rats were anesthetized as described above, weighed, and the weight of each rat was recorded. The rats were sacrificed by cardiac puncture and autopsied. Gross observation of various organs and implantation sites were made at the time of autopsy. These organs were than removed, weighed, and fixed in buffered formaldehyde 4%. The tissues collected included: heart, brain, liver, spleen, lungs, thymus, and kidney. In addition, the local implant sites were removed and fixed in buffered formaldehyde 4%. All tissues were sectioned and stained with hematoxylin and eosin and examined microscopically.

Biodegradation and Elimination

During autopsy, the polymer implant was taken out, dissolved in chloroform, dried with anhydrous magnesium sulfate, filtered, and the organic solvent was evaporated. The obtained residue was weighed and examined by IR for anhydride and ester content, GPC for molecular weight determination and NMR for RA to SA ratio. The aliquots of the degraded polymer matrix were hydrolyzed with 1 N aqueous KOH, acidified with concentrated HCl, and the liberated oil residue was extracted with ethyl acetate. The organic layer was dried with anhydrous magnesium sulfate, filtered and the solvent was evaporated to dryness. The products of polymer hydrolysis were examined for content of ricinoleic acid and sebacic acid using HPLC.

Results and Discussion

Histopathological evaluation was performed on the tissue surrounding the injected polymer after injection of the blank polymer. The blank polymer was surrounded by a thin capsule, with no evidence of any active inflammatory reaction or tissue irritation extending beyond the local capsule noted for all polymers. No evidence of granulomatous foreign-body, or lymphoid cell aggregation was noted, indicating tolerability, and lack of immunological stimulation. The blood chemistry was identical to the control groups with no signs of systemic toxicity. No signs of local irritation at the injection site were observed. The size of the implants of groups C and D remained the same as at time of injection, while for group B (PRASA-polyester-anhydride) a decrease in implant size of about 20% was noted after 42 days. For all polymer-implanted groups, the polymer remained at the injection site and formed a semisolid material that could be isolated.

The details of the biocompatibility study in rats with group B are as follows:

Two separate groups of rats were included in this study.

1. The first group consists of SD rats that received four injections of polymer blank. Two injections, 200 μl each, were subcutaneous on the opposite dorsal sides each. Two others, 50 μl each, were done intramuscularly in the femoral muscle of each leg. One implantation was used for biodegradation assessment, second implantation for histopathology evaluation. Organs of rats were selected randomly for evaluation of systemic toxicity.

2. The second group consists of Wistar rats that received 10 μl of polymer blank intracranial. The polymer was injected through a hole in the cranium made over the left parietal region with its center 5.5 mm behind the coronal structure and 3.5 mm lateral to the sagittal structure. The injections were performed with 25 μl syringe and the deepness of needle insertion was 4 mm from the coronal surface.

The experimental design is summarized in Table 6.

The biocompatibility of each tissue was graded by 5 grades from excellent tolerance to intolerance as follows:

5—Excellent tolerance (No or minimal inflammatory reaction)

4—Good tolerance (minimal adverse reaction, minimal inflammation)

3—Moderate tolerance (moderate degree of inflammation)

2—Not good tolerance (adverse reaction, inflammatory reaction)

1—Intolerance (severe necrosis and inflammatory reaction)

Results

All animals were healthy and gained weight similar to the control animals. No adverse effect or swellings were recognized at the implant sites, while the injected polymer felt solid when touching the site. All organs separated from the animals of the study were normal and no difference was found among the control and the polymer groups. Histopathology of the injection/implant site tissues indicated some acute inflammation and some necrosis at the 3 day time point with the adverse reaction confined to the injection site and tissues that are within a few millimeters from the polymer. At day 7, all implant sites showed minimal to moderate inflammation with significant improvement compared to day 3 sites. At day 21 and 42, excellent tolerability was detected. These histopathology results are similar to the results previously reported for the compatibility of the clinically used biodegradable polyesters and polyanhydrides. With regard to brain compatibility, all animals in all time points, including the day 3 time point, presented excellent biocompatibility.

Example 4

Effect of Ultrasound on Polymer Degradation

The effect of ultrasound on the degradation of polymers and the release rate of incorporated molecules within those polymers was examined. Up to a 4-fold reversible increase in the degradation rate and up to 10-fold reversible increase in release rate of incorporated molecules were observed with biodegradable polyester-anhydrides, and polylactides when exposed to ultrasound. The release rate increased in proportion to the intensity of ultrasound. Temperature and mixing were relatively unimportant in effecting enhanced polymer degradation, whereas cavitation appeared to play a significant role. Increased release rates were also observed when ultrasound was applied to biodegradable polymers implanted in rats. Histological examination revealed no differences between normal rat skin and rat skin exposed to ultrasonic radiation for 1 hr.

TABLE 6

Experimental Design

| Group | Number of rats | Implantation side | Treatment | Comment |
|---|---|---|---|---|
| 1 | 16 (4 time points, 4 rats for each time point), 4 time points: 3 days, 7 days, 21 days and 42 days | Subcutaneous two sides, Intramuscular two sides | Subcutaneous: 200 μl each side Intramuscular: 50 μl each side | Rats were anesthetized with chloral hydrate 5% solution, 0.64 ml/100 gr, shaved, the injection side was disinfected with 70% ethanol |
| 2 | 12 (3 time points, 4 rats for each time point), 3 time points: 7 days, 14 days, and 21 | Intracranial | 10 μl | |

The ultrasound probe was applied to a shaven site above an aquasonic gel, which was applied to the treated area, and the rats were exposed for 20 min to ultrasound (pulsed mode, 50% duty cycle, 5 W/cm2). For histological evaluation, the rats exposed to ultrasound were killed by asphyxiation with carbon dioxide. Sections were fixed in 10% neutral buffered formalin and evaluated by hematoxylin and eosin staining.

In Vivo Experiments

Rats (Sprague-Dawley, 200-250 g) were anesthetized with methoxyfluorane. Their abdominal and cervical fur was shaved with an electric animal hair clipper and the shaved area was cleaned with Betadine solution. Liquid polymers, PRASA, PCLCO and PLACO (0.05 ml) were injected subcutaneously and the animals exposed to ultrasound wave using a portable probe (Vibra Cell 250 (20 kHz; Sonics and Materials, Danbury, Conn.). An RAI Research (Hauppauge, Long Island, N.Y.) model 250 ultrasonic bath was used for in vitro release studies (75 kHz).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of repairing or augmenting soft tissue, the method comprising administering to a patient at a site for repair or augmentation an effective amount of an injectable biocompatible, biodegradable polymer composition, wherein said composition is stable for a period of 6 to 24 months in the soft tissue, said composition comprising
   (a) a copolymer comprising:
      (i) a first monomer which is castor oil, and
      (ii) a second monomer derived from a polyfunctional organic molecule, wherein the polymer is a liquid or paste at room temperature, and wherein the polymer increases its viscosity when exposed to physiological fluids, wherein said polyfunctional organic molecule is selected from the group consisting of lactic acid, a lactone and sebacic acid, and wherein a ratio of lactic acid to castor oil is no greater than 60:40; or
   (b) particles comprising a polymer stereocomplex, wherein the stereocomplex comprises block copolymers comprising stereoregular segments of D-lactic acid and L-lactic acid, wherein the D-Lactic acid block and the L-lactic acid block comprises at least 10 monomer units and wherein the copolymer is selected from the group consisting of poly(D-lactide-co-castor oil), poly(L-lactide-co-castor oil), poly(DL-lactide-co-castor oil), poly(caprolactone-castor oil), (PCLCO), poly(lactic acid-castor oil) (PLACO), and combinations thereof.

2. The method of claim 1, wherein the tissue to be repaired or augmented is skin.

3. The method of claim 1, wherein the polymer is injected into facial soft tissue to provide facial contouring.

4. The method of claim 1, wherein the polymer is used to repair or augment a defect in facial tissue, the defect selected from the group consisting of scars, depressions, irregularities, asymmetry in facial hemiatrophy, second bronchial arch syndrome, facial lipodystrophy, wrinkles and facial eminences.

5. The method of claim 1, wherein the tissue to be repaired or augmented is the sphincter muscle.

6. The method of claim 1, wherein the tissue to be repaired or augmented is the urinary bladder.

7. The method of claim 6 wherein polymer is administered to treat urinary incontinence.

8. The method of claim 6 wherein the polymer is administered to treat vesicoureteral reflux.

9. The method of claim 1, wherein the polymer is administered as a treatment for lip augmentation, filling or shaping.

10. The method of claim 1, wherein the polymer is administered for cheek enhancement.

11. The method of claim 1, wherein the polymer is administered as a permanent implant filler for breast augmentation.

12. The method of claim 1, wherein the polymer is administered as a permanent filler or tissue expander for the creation of extra tissue for surgical flaps.

13. The method of claim 1, wherein said composition does not feature an additional active ingredient.

* * * * *